(12) United States Patent
Gerits et al.

(10) Patent No.: US 7,685,863 B2
(45) Date of Patent: Mar. 30, 2010

(54) DEVICE FOR MEASURING THE GAS CONTENT IN A MOLTEN METAL

(75) Inventors: Erik Gerits, Genk (BE); Jacques Plessers, Houthalen-Helchteren (BE); Jos Swennen, Meeuwen-Gruitrode (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 207 days.

(21) Appl. No.: 11/908,007

(22) PCT Filed: Feb. 27, 2006

(86) PCT No.: PCT/EP2006/001765

§ 371 (c)(1),
(2), (4) Date: Sep. 7, 2007

(87) PCT Pub. No.: WO2006/094668

PCT Pub. Date: Sep. 14, 2006

(65) Prior Publication Data

US 2008/0196476 A1    Aug. 21, 2008

(30) Foreign Application Priority Data

Mar. 9, 2005    (DE) .................. 10 2005 011 181

(51) Int. Cl.
*G01N 33/20* (2006.01)
(52) U.S. Cl. .............. 73/19.07; 204/422; 204/424; 205/783.5; 205/786.5
(58) Field of Classification Search .............. 73/19.07; 204/422, 424; 205/790, 783.5, 786.5
See application file for complete search history.

(56) References Cited

U.S. PATENT DOCUMENTS 6,216,526 B1    4/2001    Junker et al.

FOREIGN PATENT DOCUMENTS

| DE | 24 23 783 A1 | 12/1975 |
| DE | 38 74 423 T2 | 2/1993 |
| EP | 0 295 798 A1 | 12/1988 |
| WO | 88/07197 A1 | 9/1988 |

OTHER PUBLICATIONS

"Spinel." (1992). In Academic Press Dictionary of Science and Technology. Oxford: Elsevier Science & Technology.*

* cited by examiner

*Primary Examiner*—Lisa M Caputo
*Assistant Examiner*—Punam Patel
(74) *Attorney, Agent, or Firm*—Panitch Schwarze Belisario & Nadel LLP

(57) ABSTRACT

A device is provided for measuring the gas content in a molten metal, the device including an immersion end having a gas-collecting body, a gas supply line opening on the immersion end, and a gas discharge line for the gases passing through the gas-collecting body. The gas-collecting body contains materials, which in contact with the molten metal do not form liquid reaction products.

7 Claims, 1 Drawing Sheet

DEVICE FOR MEASURING THE GAS CONTENT IN A MOLTEN METAL

CROSS-REFERENCE TO RELATED APPLICATIONS

This application is a Section 371 of International Application No. PCT/EP2006/001765, filed Feb. 27, 2006, which was published in the German language on Sep. 14, 2006, under International Publication No. WO 2006/094668 A1 and the disclosure of which is incorporated herein by reference.

BACKGROUND OF THE INVENTION

The invention relates to a device for measuring the gas content in a molten metal, the device comprising an immersion end having a gas-collecting body, a gas supply line opening to the immersion end, and a gas discharge line for the gases passing through the gas-collecting body, and a method of using the device.

Such devices are known from European Patent EP 307 430 B1. The devices described here are suitable for measuring the gas content, particularly hydrogen, for example in molten steel. Here, the gas-collecting body is made of porous stone. With different melts it can happen that the measurement is impaired, in that the openings of the body become blocked or the surface of the body does not make sufficient contact with the molten metal.

A similar device is also known from U.S. Pat. No. 6,216, 526 B1. This device has a quartz-glass tube, in which the melt is collected. The molten metal can then penetrate into the interior of the immersion probe through a stopper, which is permeable for the melt. This stopper made of aluminum oxide should hold back impurities in the molten metal.

From European Patent DE 38 74 423 T2 (EP 295 798 B1) a probe is known for determining the concentration of a gas in molten metal, the probe comprising a gas-collecting body, wherein the gas-collecting body has a gas supply line and a gas discharge line for the gases passing through the gas-collecting body. The gas-collecting body is made of aluminum oxide. From German published patent application DT 24 23 783 A1, an immersion sensor is known for measuring oxygen in molten metals with a solid electrolyte spinel structure.

BRIEF SUMMARY OF THE INVENTION

The invention is based on the problem of improving the present devices and, in particular, preventing a blockage of the gas-collecting body.

The problem is solved according to the invention by a device for measuring the gas content in a molten metal, comprising an immersion end having a gas-collecting body, a gas supply line opening at the immersion end, and a gas discharge line for the gases passing through the gas-collecting body, wherein the gas-collecting body contains such materials, which in contact with the molten metal do not form liquid reaction products, characterized in that the materials not forming liquid reaction products form at least a part of the surface of the gas-collecting body as a surface layer, which is provided for contact with the molten metal, and that the surface layer has a thickness of approximately 0.3 to 5 mm.

Because the gas-collecting body contains such materials, which in contact with the molten metal do not form liquid reaction products, the surface of the gas-collecting body therefore cannot be occupied with foreign materials, such that the contact of the molten metal with the gas-collecting body is guaranteed, and thereby allowing a gas exchange. In particular, it is advantageous that the portion of materials, which in contact with the molten metal do not form liquid reaction products, equals at least 80 wt. %, preferably at least 90 wt. %, relative to the gas-collecting body. In addition, it is useful that the gas-collecting body is a porous body, wherein the porosity preferably equals approximately 50%.

Advantageously, the gas-collecting body contains magnesium oxide and/or aluminum oxide and/or chromium oxide. In particular, the gas-collecting body can contain a material of the formula $AB_2O_4$, where A is a metal preferably from the group Mg, Fe, and Mn, and B is another metal preferably from the group Al, Cr, Fe, and V. The material of the formula $AB_2O_4$ has a spinel structure. This can already exist in the unused gas-collecting body or can be formed from material of the gas-collecting body for the first time when immersed or during the presence of the gas-collecting body in the molten iron or steel. For forming the $AB_2O_4$ structure, the metals above-named can preferably be used.

According to the invention, the materials not forming liquid reaction products form at least part of the surface of the gas-collecting body as a surface layer, namely at least a part of the surface of the gas-collecting body, which is provided for contact with the molten metal. The surface layer has a thickness of approximately 0.3 to 5 mm.

The device can be used according to the invention in molten steel with an oxygen content of at least 100 ppm and/or a content of sulfur and/or magnesium and/or silicon of at least 0.1 wt. %. The device can also be used according to the invention for measuring hydrogen, nitrogen, carbon monoxide, and/or carbon dioxide in molten steel.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there is shown in the drawing an embodiment which is presently preferred. It should be understood, however, that the invention is not limited to the precise arrangements and instrumentalities shown. In the drawings.

DETAILED DESCRIPTION OF THE INVENTION

Figure 1:
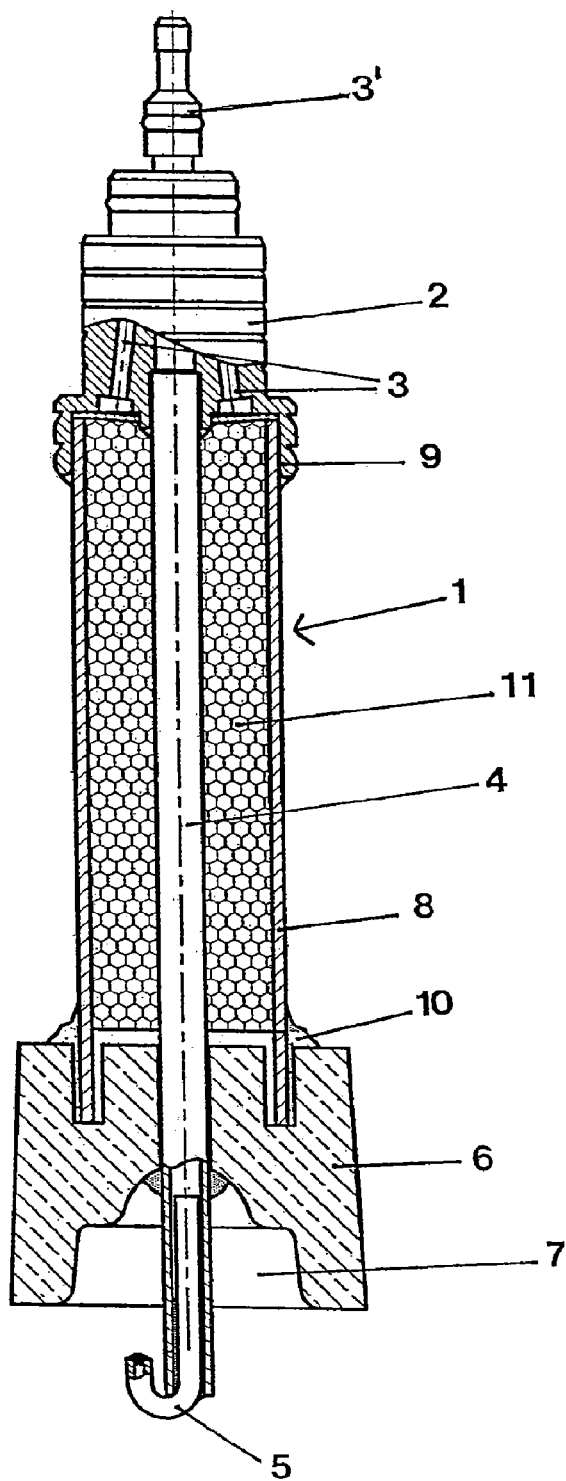
FIG. 1 is a longitudinal side view, partially in cross-section, of the immersion end of one embodiment of a device according to the invention.

The basic construction of a device for measuring the gas content in molten metal is known, for example, from European Patent EP 307 430 B1. FIG. 1 of EP 307 430 B1, in connection with the description, shows the measurement construction including the immersion end with a gas-collecting body. The present invention can also relate back to this basic construction. The measurement process is likewise described, for example in EP 307 430 B1.

The immersion end 1 is connected to an attachment nozzle 2 with a carrier tube, with whose help the immersion process is performed. The attachment nozzle contains several gas connections 3; 3', wherein the centrally arranged gas connection nozzle 3' introduces carrier gas into the molten metal through a gas supply line 4. The gas supply line 4 is composed essentially of a quartz tube, which opens at its immersion end into a further, bent quartz tube 5, whose opening is oriented in the direction of the gas-collecting body 6. The gas-collecting body 6 has a bell-shaped recess 7 around the gas supply line 4. The opening of the quartz tube 5 is oriented toward the recess 7, so that the gas stream flows out of the supply line 4 toward the recess 7. Here, gas is collected from the molten metal and guided with the carrier gas by the body of the immersion end 1 toward the gas connections 3. From there, transmission continues to the corresponding measurement devices.

Between the attachment nozzle 2 and the gas-collecting body 6 the immersion end 1 has a quartz tube 8, which is fixed on the attachment nozzle 2 and on the gas-collecting body 6 by bonding agent 9 or cement 10. The quartz tube 8 is filled with aluminum oxide 11, which, first, fixes the gas supply line 4 and, second, allows the transmission of the carrier gas with the gas to be measured.

The gas-collecting body 6 is made of $MgAl_2O_4$ and an organic binding agent. It has a porosity of approximately 50%, so that the gas from the molten steel can be collected. The average pore diameter equals approximately 40 μm. The composition of the gas-collecting body guarantees that the pores are not blocked or covered in any way, but instead remain open, so that the gas can penetrate in an unimpaired way.

In another example, the gas-collecting body 6 is formed from pressed and sintered $Al_2O_3$-corundum, after which it is immersed and impregnated in an aqueous MgO suspension, whereby a surface layer is produced. The gas-collecting body 6 is then dried. The thickness of the surface layer equals approximately 0.3 to 5 mm, preferably 1 to 3 mm, after the treatment. The layer is not shown in the drawing.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A device for measuring gas content in a molten metal, the device comprising an immersion end having a gas-collecting body, a gas supply line opening at the immersion end, and a gas discharge line for gases passing through the gas-collecting body, wherein the gas-collecting body contains materials, which in contact with the molten metal do not form liquid reaction products, wherein a portion of the materials which do not form liquid reaction products form at least a part of a surface of the gas-collecting body as a surface layer, which is provided for contact with the molten metal, and wherein the surface layer has a thickness of approximately 0.3 to 5 mm; and wherein one of the materials comprises a material which converts to $AB_2O_4$ upon immersion of the device into molten iron or steel, wherein A is a metal selected from the group consisting of Mg, Fe and Mn, and B is a further metal selected from the group consisting of Al, Cr, Fe, and V.

2. The device according to claim 1, wherein the portion of materials, which in contact with the molten metal do not form liquid reaction products, equals at least 80 wt. % relative to the gas-collecting body.

3. The device according to claim 2, wherein the portion of materials, which in contact with the molten metal do not form liquid reaction products, equals at least 90 wt. % relative to the gas-collecting body.

4. The device according to claim 1, wherein the gas-collecting body is a porous body.

5. The device according to claim 1, wherein the gas-collecting body contains at least one oxide selected from the group consisting of magnesium oxide, aluminum oxide and chromium oxide.

6. A method for measuring a gas content in molten steel having an oxygen content of at least 100 ppm and/or a content of at least one of sulfur, magnesium and silicon of at least 0.1 wt. %, the method comprising immersing the immersion end of the device of claim 1 in the molten steel.

7. A method for measuring a gas content of at least one of hydrogen, nitrogen, carbon monoxide, and carbon dioxide in molten steel, the method comprising immersing the immersion end of the device of claim 1 in the molten steel.

* * * * *